(12) United States Patent
Guerra

(10) Patent No.: US 6,978,169 B1
(45) Date of Patent: Dec. 20, 2005

(54) PERSONAL PHYSIOGRAPH

(76) Inventor: Jim J. Guerra, 2450 Oak Hill Cir. #431, Fort Worth, TX (US) 76108

( * ) Notice: Subject to any disclaimer, the term of this patent is extended or adjusted under 35 U.S.C. 154(b) by 530 days.

(21) Appl. No.: 10/116,995

(22) Filed: Apr. 4, 2002

(51) Int. Cl.$^7$ ............................................. A61B 5/044
(52) U.S. Cl. ..................................................... 600/523
(58) Field of Search ................................ 600/523, 522, 600/509, 525, 508, 512, 513, 515; 128/920

(56) References Cited

U.S. PATENT DOCUMENTS

| | | | | |
|---|---|---|---|---|
| 4,679,144 | A | * | 7/1987 | Cox et al. .................... 600/516 |
| 4,794,532 | A | * | 12/1988 | Leckband et al. ........... 600/515 |
| 5,159,932 | A | * | 11/1992 | Zanetti et al. ............... 600/508 |
| 5,309,920 | A | * | 5/1994 | Gallant et al. ............... 600/523 |
| 5,447,164 | A | * | 9/1995 | Shaya et al. ................. 600/523 |
| 5,876,351 | A | * | 3/1999 | Rohde .......................... 600/523 |
| 6,551,252 | B2 | * | 4/2003 | Sackner et al. .............. 600/536 |
| 2003/0073915 | A1 | * | 4/2003 | McLeod et al. .............. 600/509 |

* cited by examiner

*Primary Examiner*—Jeffrey R. Jastrzab
(74) *Attorney, Agent, or Firm*—Fulbright&JaworskiLLP

(57) ABSTRACT

Disclosed are systems and methods which provide a relatively small, preferably easily transportable, interpretive biotelemetric monitor, such as may utilize platforms developed for use as personal digital assistants, adapted for use by non-health care personnel. A preferred embodiment biotelemetric monitor comprises a self-contained EKG monitor providing ICU cardiac monitoring with accurate real-time diagnostic heart rhythm analysis directly to the wearer. Preferred embodiment biotelemetric monitors implement multiple interactive screens to guide a user through a series of screens to help understand the monitored conditions. Moreover, the biotelemetric monitor may operate to analyze and interpret the monitored data to thereby present information with respect to the probable implications of the monitored condition and/or make recommendations which may be useful to the patient at that time. Preferably, communications functionality is included to facilitate communication between the biotelemetric monitor and a host system.

9 Claims, 5 Drawing Sheets

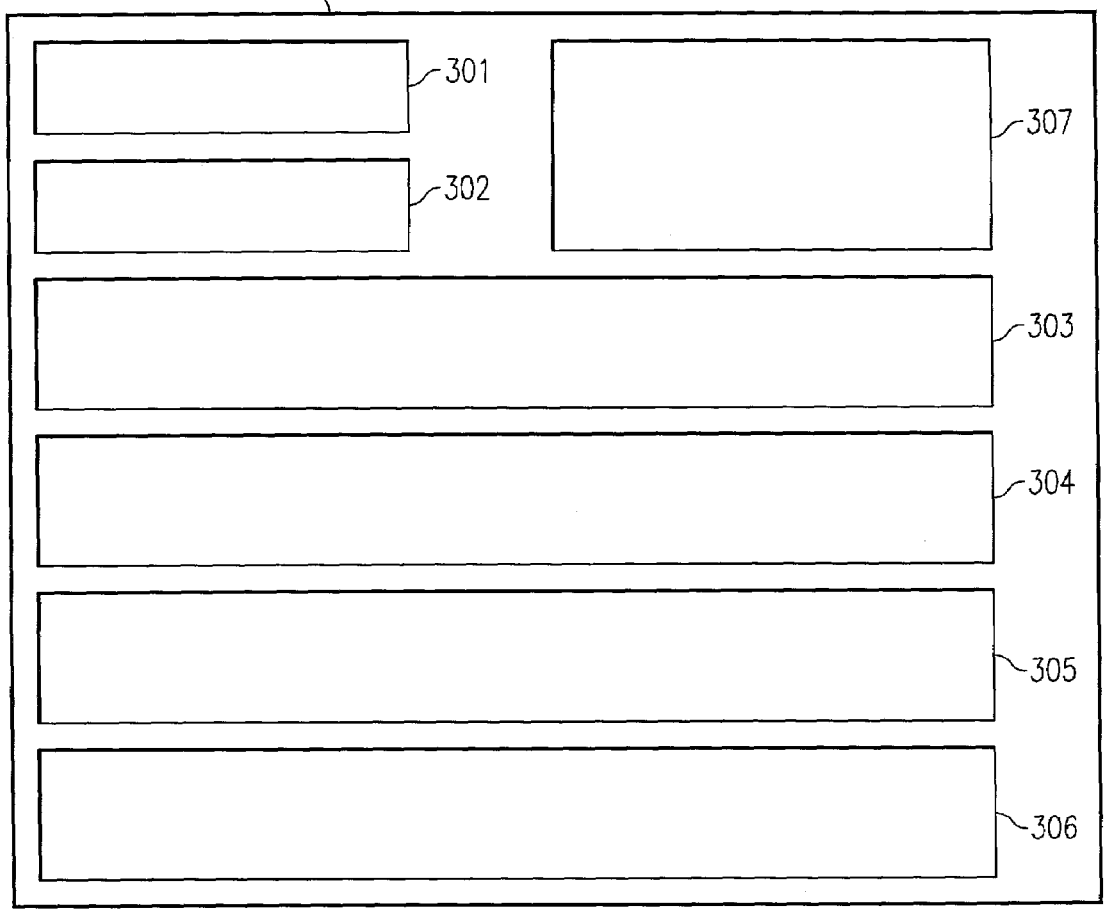

```
HEART RATE ─ 401
  MONITORED_DATA = HR
402A            MIN_HR_FOR_PERIOD
                MAX_HR_FOR_PERIOD
402B ─ STATUS = "NORMAL" IF 60 < HR < 100
                "TACHY CARDIA" IF HR>100
                "BRADY CARDIA" IF HR<60
403 ─ INFORMATION = "THE RATE AT WHICH THE HEART BEATS -
                EQUAL TO THE PULSE AND VARIES IN RESPONSE
                TO PHYSICAL AND EMOTIONAL ACTIVITY"
404 ─ SYMPTOMS = EXCERPT HEART RATE SYMPTOMS FROM REFERENCE
                PRESENT JUMP TO HEART RATE IN REFERENCE
405 ─ CAUSES = EXCERPT HEART RATE CAUSES FROM REFERENCE
                PRESENT JUMP TO HEART RATE IN REFERENCE
406 ─ RECOMMENDATION = "CONSULT PHYSICIAN" IF HR < 60
                "NO ACTION RECOMMENDED" IF 100 < HR < 130
                "RECORD EVENT" IF 100 < HR < 130 AND IF
                CORRELATION_WITH_SYMPTOMS = "SHORTNESS OF BREATH"
                "RECORD EVENT AND ACCESS DIAGNOSIS WIZARD"
                IF 100 < HR < 130 AND IF
                CORRELATION_WITH_SYMPTOMS = "DIZZYNESS"
                "CONSULT PHYSICIAN" IF HR > 130
                AND IF CORRELATION_WITH_SYMPTOMS = NULL
408 ─ CORRELATE HEART RATE WITH PULSE FOR FIBRILATION
                INTERPRETATION
409 ─ CORRELATE HEART RATE WITH SYMPTOMS ACKNOWLEDGED
                BY USER FOR HISTORICAL DATABASE, INTERPRETATION BY
                SYSTEM, AND/OR ANALYSIS BY TRAINED PROFESSIONAL
407 ─ UTILIZE NAVIGATION TOOL BOX
```

FIG. 4

PERSONAL PHYSIOGRAPH

TECHNICAL FIELD OF THE INVENTION

The invention relates generally to biotelemetry and, more particularly, to monitoring, displaying, analyzing, and recording biotelemetric data.

BACKGROUND OF THE INVENTION

Various devices have been developed to observe, monitor, and/or record biotelemetry data for use in diagnosis and treatment of an individual. For example, electrocardiograms (EKGs) have been developed to monitor the electrical activity associated with a beating heart. By attaching electrical transducers to an individual at particular locations, an EKG may be utilized to provide graphical traces of heart activity. These graphical traces may include specific relevant portions, such as a P wave, QRS complex, T wave, U wave, P-R segment, S-T segment, PR interval, and QT interval, each useful in providing particular diagnostic information.

However, such EKGs have typically been very expensive and complex devices. For example, in order to provide all the information described above, EKGs have typically employed 12 leads, where leads are various combinations of signal paths associated with transducer electrodes placed upon the body.

Three of these leads, usually designated as leads I, II and III, are bipolar (i.e., they detect a change in electric potential between two points) and detect an electrical potential change in the frontal plane. Specifically, lead I is between a right arm electrode and a left arm electrode, the left arm electrode being positive. Lead II is between the right arm electrode and a left leg electrode, the left leg electrode being positive. Lead III is between the left arm electrode and the left leg electrode, the left leg electrode again being positive. The same three electrodes providing leads I, II and III discussed above are also typically used to form three unipolar leads, known as the augmented leads. These three augmented leads are referred to as aVR (right arm), aVL (left arm) and aVF (left leg), and also record a change in electric potential in the frontal plane. These augmented leads are unipolar in that they measure the electric potential at one point with respect to a null point (one which does not register any significant variation in electric potential during contraction of the heart). This null point is typically obtained for each lead by adding the potential from the other two leads. Additionally, six unipolar leads, each in a different position on the chest and monitoring electrical variations that occur directly under the electrode, record the electric potential changes in the heart in a cross sectional plane.

Properly placing this number of leads is often difficult, requiring the assistance of a trained professional. Additionally, equipment for monitoring all 12 leads and providing output of information with respect thereto typically must be complex. Moreover, the information provided by such prior art 12 lead EKGs typically requires reading by a trained professional in order to provide useful diagnostic information.

In addition to the complexity generally associated with the use of 12 leads, typical EKGs have additional functionality associated therewith, such as may be useful to professionals utilizing the EKG. For example, EKGs typically are adapted to monitor additional biotelemetry attributes, such as oxygen saturation. EKGs also generally include added functionality, such as including a cardiac defibrillator, a graph printer, and the like.

As can be readily appreciated from the above, prior art EKGs are typically provided in a relatively large, complex, and expensive form factor. Although not objectionable in a typical health care provider setting, such as a clinic or hospital, such EKGs are typically not widely available due to such size, complexity, and/or expense related considerations. For example, because of their size and expense, cardiac patients typically do not have availability of EKG machines in their home or office for monitoring and diagnostic purposes. Accordingly, a cardiac patient, or any individual who suspects a heart related anomaly, must typically present himself at a hospital emergency room, or other health care provider facility, in order to have access to an EKG machine for monitoring and diagnosis. Moreover, even if a typical prior art EKG machine were available to such a patient, such as in the patient's home or office, the use of such a device by the patient would be of limited usefulness as the information presented by the EKG would still require interpretation by a trained professional.

Accordingly, a vast amount of time and money are needlessly wasted each year in association with the limited availability of such biotelemetric machines. For example, patients with cardiac type symptoms, such as tightness in the chest, shortness of breath, light headedness, etcetera, must wait in a crowded hospital emergency room or clinic to be placed upon an EKG machine for monitoring and pay the services of a physician and for the use of the EKG machine only to discover that a benign condition, such as a gastrointestinal anomaly, was the cause.

Some attempts have been made to address problems associated with such limited availability of such biotelemetric machines, resulting in such devices as the Holter monitor and various forms of event recorders. However, these devices are themselves not without disadvantages.

The Holter monitor, for example, was initially developed as a 75 pound backpack to be worn by a patient to record the EKG of the wearer and transmit the signal to a host system. Since its introduction, the device has been greatly reduced in size, providing a more portable form factor, allowing for more freedom of movement with respect to its wearer. However, the use of a typical Holter monitor does not provide its wearer with information, but rather digitally records the EKG information for downloading and analysis by a trained professional at a later time.

Similarly, typical event recorders available today do not provide information to a user, but rather simply record an event for later analysis by a trained professional. For example, EKG recording by an event recorder may be initiated as the patient experiences particular symptoms in order to record the EKG coincident with the symptoms. This recorded information may be downloaded for analysis by a trained professional, possibly with notes by the patient as to the particular symptoms experienced at that time, at a later time.

Accordingly, a need exists in the art for acquisition, presentation, and/or analysis of biotelemetry data in real-time to a patient. A further need exists in the art for machines providing such biotelemetry data to be portable and relatively inexpensive to facilitate their deployment and widespread use by ambulatory patients.

BRIEF SUMMARY OF THE INVENTION

The present invention is directed to systems and methods which provide a relatively small, preferably easily transportable, interpretive biotelemetric monitor adapted for use by non-health care personnel. A preferred embodiment of the present invention comprises a self-contained EKG monitor providing ICU cardiac monitoring with accurate real-time diagnostic heart rhythm analysis directly to the wearer.

Preferred embodiment EKG monitors of the present invention comprise a small, portable, user-friendly, microprocessor controlled unit using multiple interactive screens, such as may implement touch screen technology, to guide a user through a series of screens to help the patient understand the monitored conditions. For example, an EKG monitor of the present invention may monitor various electrodes coupled to the user to present the user with information as to the user's current rhythm. Moreover, the microprocessor, and associated instruction set of the present invention, may operate to analyze and interpret the monitored data, perhaps utilizing a historical database of data monitored from the user and/or known comparative data, to thereby present information with respect to the probable implications of the monitored condition and/or make recommendations which may be useful to the patient at that time.

Preferably, biotelemetric information is provided by the EKG monitor in a hierarchy of screens. For example, a highest level screen might be a monitor screen presenting information with respect to currently monitored attributes. This screen may include interpretive information, such as a general status indicator of "normal," "arrhythmia," etcetera, with respect to the monitored condition. Alarms are also preferably provided to alert the user of potentially serious conditions.

Screens further down in the hierarchy preferably provide additional detail or information. These screens are preferably navigated by a user and/or displayed upon particular events. For example, an alarm may be triggered with respect to a particular monitored attribute and presented on a high level monitor screen, such as next to a graphical representation of the monitored attribute for which the alarm has been triggered. The user may then be able to select the alarm to display a screen presenting more detailed information with respect to the condition. This screen, or perhaps screens below this screen in the hierarchy, may provide instruction to the user, such as to seek professional care immediately or to take particular action to mitigate risk of permanent injury.

Preferred embodiment EKG monitors of the present invention record monitored biotelemetric data, such as to a historical database. Accordingly, this information may be utilized in determining a user's condition, such as for comparison to a current condition to detect changes, to analyze trends, or even to provide to a health care provider for professional analysis.

Embodiments of EKG monitors according to the present invention provide functionality in addition to the aforementioned monitoring, displaying, analyzing, and recording of biotelemetric data. For example, an EKG monitor of the present invention may include communications functionality to facilitate communication between the EKG monitor and a host system, such as a computer, computer network, or telephony device of a health care professional. Such communications may utilize wired and/or wireless links. For example, a preferred embodiment EKG monitor of the present invention may be coupled to a telephone line or network link periodically to download biotelemetric data to and/or receive operational instructions or information from a computer system of the user's physician. Additionally or alternatively, an EKG monitor of the present invention may include wireless communication capability, such as that compatible with cellular type personal communication services, in order to transmit data periodically and/or real-time, such as to notify emergency personnel of a life threatening condition being monitored.

A most preferred embodiment EKG monitor of the present invention is provided in a relatively small form factor to facilitate transportability. For example, an EKG monitor of the present invention may be developed upon a relatively small, and substantially rugged, processor based platform which includes a suitably sized display screen and operates upon battery power. Such platforms have been developed for use as personal digital assistants (PDAs) and have advanced such that processing power, memory capacity, display screen size and resolution, and battery life of this technology may be leveraged in providing an EKG monitor of the present invention. For example, the "pocket PC" variety of PDA, such as may use the INTEL STRONGARM processor under control of the MICROSOFT WINDOWS CE operating system, may be adapted to provide an EKG monitor of the present invention. However, other processing platforms may be utilized according to the present invention, such as those of the PALM series of PDAs using the PALM OS.

Accordingly, it should be appreciated that a technical advantage of the present invention is that acquisition, presentation, and/or analysis of biotelemetry data is provided for in real-time to a patient. A further technical advantage of the present invention is that preferred embodiments provide a biotelemetric device which is portable and relatively inexpensive, thereby facilitating deployment and widespread use by ambulatory patients.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which:

FIG. 3 shows a block diagram of a display screen of an embodiment of the present invention;

FIG. 4 shows pseudo code for populating a display screen such as that of FIG. 3 with information according to a preferred embodiment of the present invention.

DETAILED DESCRIPTION OF THE INVENTION

Figure 1A:
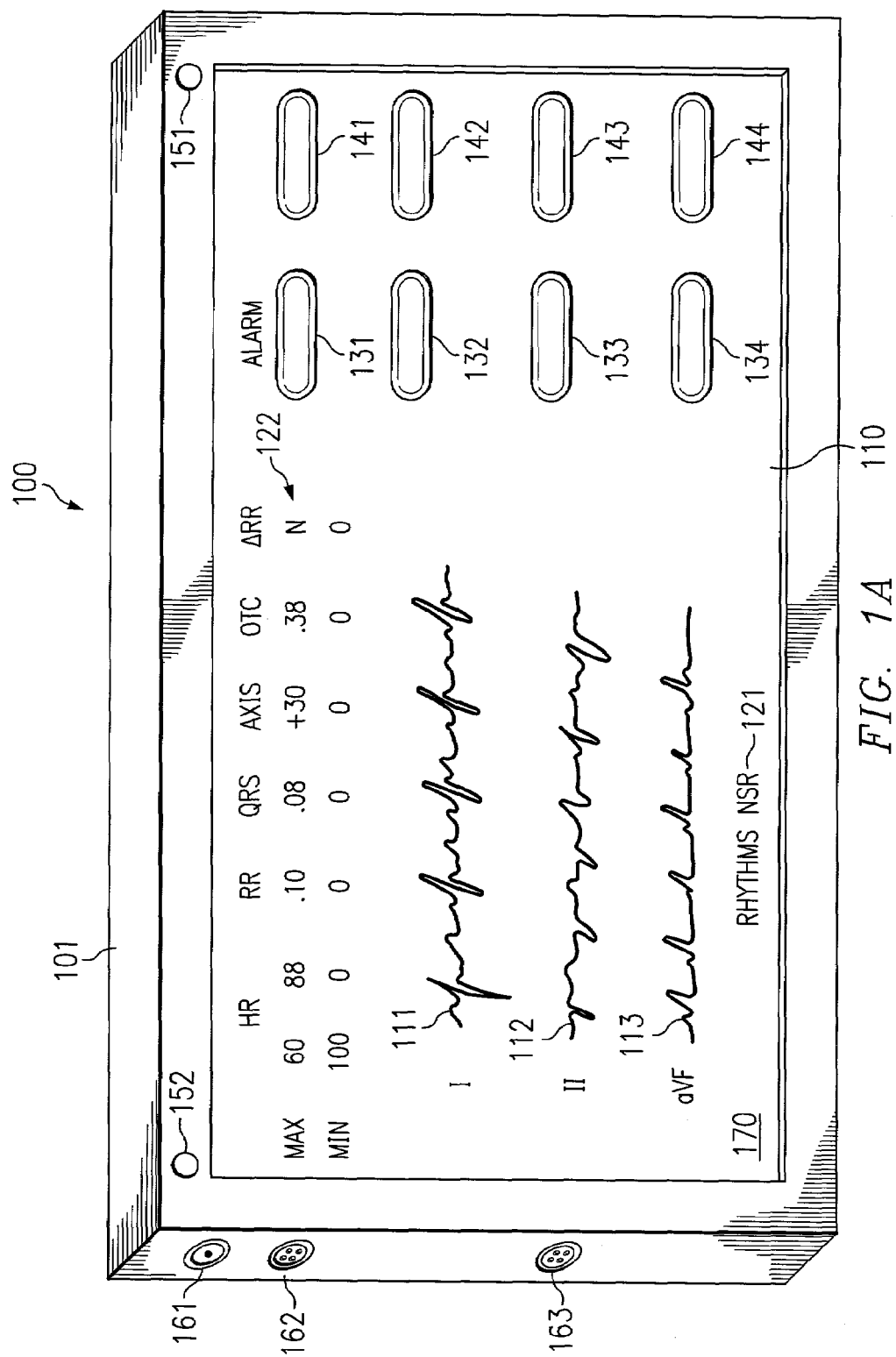
FIG. 1A shows a biotelemetry monitoring device according to a preferred embodiment of the present invention.

FIG. 1A shows a preferred embodiment biotelemetric monitoring device of the present invention as EKG monitor 100. EKG monitor 100 of the illustrated embodiment comprises case 101, which preferably presents a relatively small form factor to facilitate transportability. Case 101 is preferably rugged and water resistant. For example, case 101 may be sealed and pressurized with an inert gas, such as nitrogen, to thereby prevent infiltration by dust or water particles. Components of EKG monitor 100 are preferably disposed within case 101 in such a way as to be shock resistant. For example, resilient material, such as rubber, may be utilized at attachment points between case 101 and other components of EKG monitor 100. Case 100 of the preferred embodiment is further adapted to provide desired functionality, such as storage of wire leads and/or electrodes therein, providing couplers for accommodating belt clips and the like, providing a cover or covers to protect or hide various portions of the monitor, such as interface jacks and/or the display screen, and/or the like.

EKG monitor 100 of the illustrated embodiment further comprises display 110, which preferably presents a relatively large display screen suitable for displaying both graphical and textual information. For example, display 110 may comprise a liquid crystal display (LCD) as is well known in the art. Display 110 may be a monochromatic screen, to reduce costs associated therewith, or may be color. A back or side light may be included with display 110, to facilitate reading of information therefrom. However, any such light is preferably controllable to conserve energy and, therefore, prolong battery life for use of EKG monitor 100. Display 110 may incorporate touch screen technology, as is in wide spread use in personal digital assistants (PDAs), to facilitate user input. Of course, other user input devices, such as keyboards, thumb wheels, joysticks, buttons (whether software or hardware and whether programmable or fixed function), trackballs, pointing devices, styluses, and the like, may be used in addition to or in the alternative to the aforementioned touch screen for accepting user input, if desired.

EKG monitor 100 of the preferred embodiment is adapted to interface for accepting information, signals, input, etcetera from a number of sources. For example, as mentioned above, EKG monitor 100 is preferably adapted to interface with a user to accept input therefrom. Accordingly, EKG monitor 100 of the illustrated embodiment includes various forms of user interface buttons.

A first form of user interface button is shown as software buttons 131–134 and 141–144. These software buttons may present programmable button images upon display 110 for selection by a user, such as by touching the corresponding portion of the screen or operating a pointing device to select a desired button. The software buttons may preferably be positioned at any desired location of display 110 and may present information therein or associated therewith, such as to identify the function of the button or present an alarm condition for which the button provides a link to additional relevant information.

A second form of user interface button is shown as hardware buttons 151 and 152. For example, hardware button 151 may provide for powering EKG monitor 100 on and off. Hardware button 152 may provide an always available event record button to allow a user to initiate event recording when experiencing particular symptoms, irrespective of the status of display 110 and, therefore, the software buttons displayed thereon. For example, hardware button 152 may operate in cooperation with memory 12 to identify a portion of monitored biotelemetry data stored therein for association with the occurrence of an event as indicated by manipulation of button 152. Such cooperation may be useful in providing several minutes of data surrounding the activation of an event record button for analysis of pre and post symptomatic intervals.

It should be appreciated that the preferred embodiment hardware buttons, like the software buttons described above, may present information therein or associated therewith. For example, hardware button 151 may have a light emitting diode (LED) disposed therein to indicate a powered on state of EKG monitor 100. Further information, such as the status of the battery, may be indicated by a change in color or a flashing pattern of this LED, for example.

Further interfacing of EKG monitor 100 is preferably provided by interface ports disposed thereon. For example, EKG monitor 100 of the illustrated embodiment includes power interface 161, such as may be used to interface with an external power supply for receiving operating power and/or recharging an internal battery. EKG monitor 100 of the illustrated embodiment further includes biotelemetric probe interface port 162, such as may be utilized to interface with one or more electrodes or other probes configured to obtain biotelemetry data. Interface port 163 of the illustrated embodiment provides a data interface, such as may be utilized to couple EKG monitor 100 to a host computer system, a network, the Internet, a telephone system, a printer, a facsimile machine, and/or the like.

Although not readily apparent in the illustration of FIG. 1A, EKG monitor 100 of the preferred embodiment may include one or more additional or other interfaces for use according to the present invention. For example, EKG monitor 100 may include a wireless interface, such as a radio frequency (RF) or infra-red (IR) interface, to allow data communication without EKG monitor 100 being tethered to a host system. Wireless interfaces utilized according to the present invention are not limited to those used in establishing data communication, but may include, for example, wireless interfaces providing various functional features such as position determinations as are available with global positioning sensor (GPS) technology. Such interfaces are represented in the block diagram of EKG monitor 100 shown in FIG. 1B.

Figure 1B:
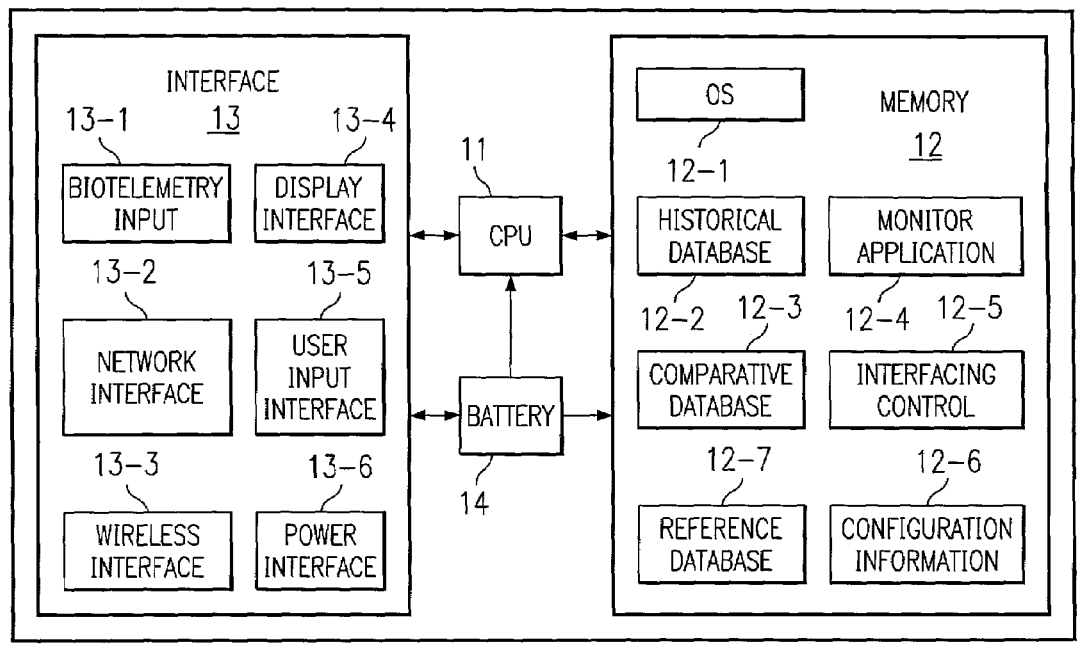
FIG. 1B shows a functional block diagram of an embodiment of the biotelemetry monitoring device of FIG. 1.

Directing attention to FIG. 1B, a functional block diagram of a preferred embodiment of EKG monitor 100 is shown. The block diagram of FIG. 1B includes three primary functional blocks of EKG monitor 100, those being central processing unit (CPU) 11, memory 12, and interface 13, each of which is provided power by battery 14.

CPU 11 may be any processor configured to operate under control of an instruction set defining operation as described herein, such as a processor from the INTEL PENTIUM family of processors or the MOTOROLA POWERPC family of processors. However, a most preferred embodiment of the present invention leverages portable processor platforms and technology already developed and, therefore, utilizes a processor from the INTEL STRONGARM family of processors developed for use in portable devices.

Memory 12 may be comprised of random access memory (RAM), read only memory (ROM), flash memory, magnetic and/or optic storage media, and/or the like. Memory 12 preferably provides storage of an instruction set (e.g., operating system 12-1, monitor application 12-4, and interface control 12-5) defining operation as described herein as well as user data (e.g., historical database 12-2) and/or other data (e.g., comparative database 12-3, configuration information 12-6, and reference database 12-7) useful therewith. For example, memory 12 may provide streaming and/or loop storage of monitored biotelemetry data.

Interface 13 may be comprised of any number of input and output devices and/or ports as well as components ancillary thereto. For example, interface 13 may provide biotelemetry input 13-1 (such as may correspond to biotelemetric probe interface 162 of FIG. 1A), network interface 13-2 (such as may correspond to interface port 163 of FIG. 1A), wireless interface 13-3, display interface 13-4 (such as may correspond to display 110 of FIG. 1A), user input interface 13-5 (such as may correspond to software buttons 131–134 and 141–144, hardware buttons 151 and 152, and/or a touch screen aspect of display 110 of FIG. 1A), and power interface 13-6 (such as may correspond to power interface 161 of FIG. 1A).

Battery 14 is preferably a rechargeable power source, such as a nickel-cadmium or lithium-ion power cell well known in the art. Accordingly, battery 14 may be relied upon to provide operational power to EKG monitor 100 when carried by the user.

EKG monitor 100 of the preferred embodiment provides interfacing for a plurality of biotelemetric probes, such as electrodes useful in monitoring electronic signals generated from the operation of heart muscles. Additional or alternative biotelemetric probes useful according to the present invention may include provide information with respect to oxygen saturation, blood pressure, respiration, muscle tension, muscle movement, ocular movement, electroencephalogram, and/or the like.

An EKG monitor of a most preferred embodiment provides a 3 lead capability. Preferably the monitor may be adjusted to read any 3 of 6 standard limb leads through 3 separate wire interfaces of the monitor. For example, the wire interfaces may be coupled to electrodes disposed at each wrist and the left ankle, and the user may choose between monitoring the I, II, and III bipolar leads or the aVR, aVL, and aVF unipolar augmented leads (it being appreciated that the leads may be placed on the wrists and ankles with the electrodes behaving as if they were at the shoulders and groin because the limbs serve as electrical conductors to these points). Alternatively, the 3 leads of the preferred embodiment may be any 3 of the 6 unipolar chest leads, or any other combination of leads chosen by the user.

Although discussed above with respect to wireline interfacing of various leads utilized to monitor biotelemetry according to the present invention, it should be appreciated that the present invention is not limited to the use of such wireline tethers. For example, wireless probes, such as may utilize a radio frequency (RF) protocol such as BLUETOOTH or IEEE 802.11 or a light frequency such as an infrared (IR) protocol, may be utilized according to the present invention. In such an embodiment EKG monitor 100 may easily be transported in a purse, satchel, or backpack of the user or, perhaps, even left stationary while the user remains within an operational area of the particular probes utilized.

Preferably, biotelemetric information is provided by EKG monitor 100 in a hierarchy of screens. A highest level screen may present high level information with respect to operation of EKG monitor 100, such as to show the biotelemetric data being monitored, provide operational control of the monitor, and/or provide user interfacing to facilitate intuitive navigation of the screens of the hierarchy. Lower level screens may present more detailed information, perhaps making recommendations to a user with respect to a monitored condition, provide particular selected categories of information, and/or provide user interfacing to facilitate intuitive navigation of the screens of the hierarchy. For example, a user may navigate from a first screen presenting high level data and/or a broad overview of monitored data, following the hierarchy, to arrive at secondary screens giving the basic interpretation, perhaps including definitions, and from there further information may be accessed as far as symptoms, causes, recommendations, course of action, need for medical attention, etcetera.

Similarly, one or more screens of the preferred embodiment hierarchy may be utilized to solicit information from a user. For example, a user may activate an event recorder button to cause EKG monitor 100 to identify, and perhaps isolate, monitored information for a period of time, preferably pre and post activation of the button, for analysis. This operation may be accompanied by a screen or series of screens soliciting symptom information from the user to be associated with the recorded event, such as for use in analysis or diagnosis. For example, a symptom "wizard" process may be activated to intelligently query the user, preferably interacting to present appropriate questions responsive to input by the user and/or monitored biotelemetric information.

Figure 2:
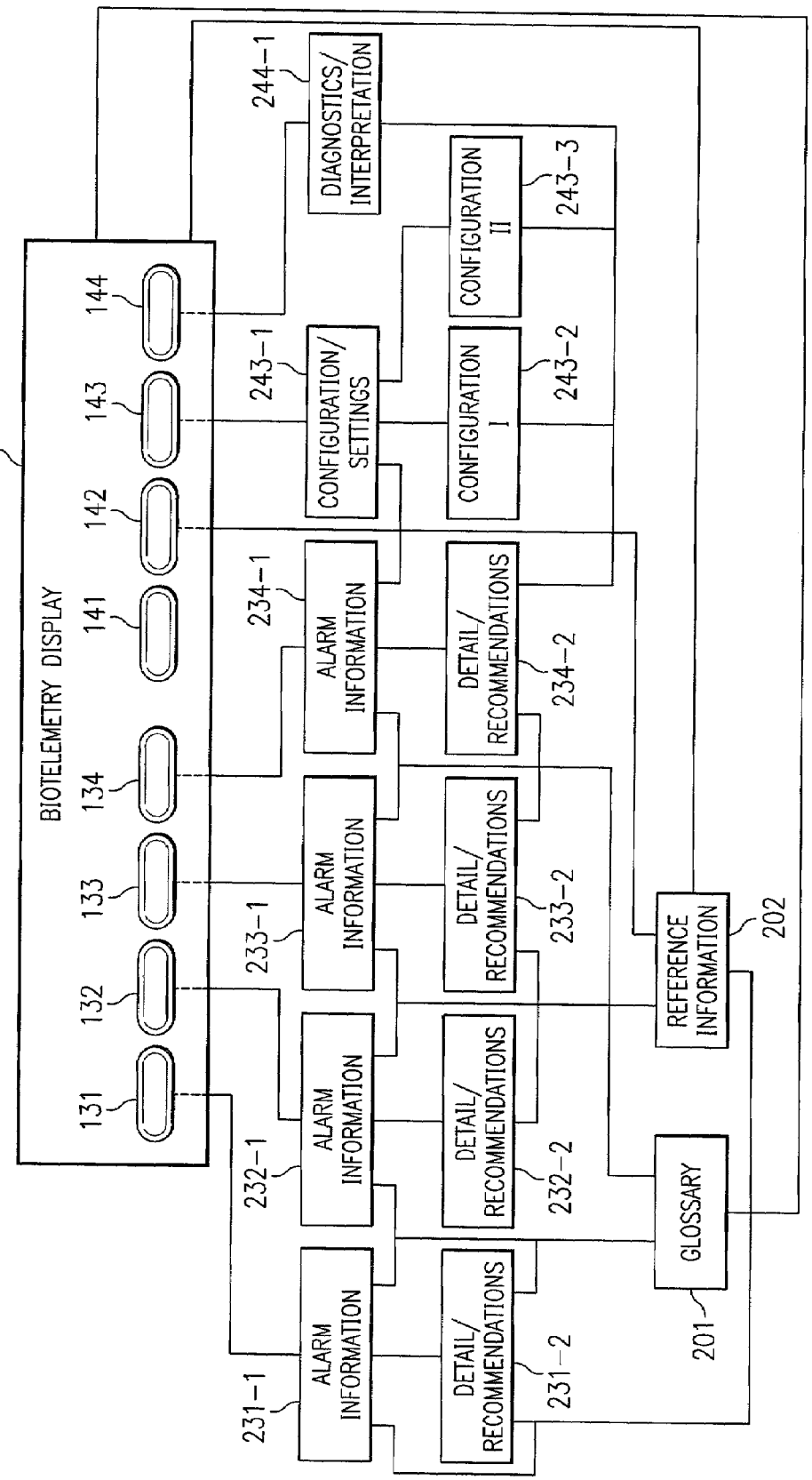
FIG. 2 shows a display screen hierarchy of a biotelemetry monitoring device according to a preferred embodiment of the present invention.

An illustrative embodiment of a screen hierarchy is represented in FIG. 2, wherein highest level screen 170 of FIG. 1A is linked to various lower level screens providing more detailed information and/or selected operational functions. Accordingly, various buttons operational with respect to screen 170 may present particular associated lower level screens when operated. For example, operation of software buttons 131–134, which in the preferred embodiment are associated with alarms, may result in EKG monitor 100 displaying a corresponding one of alarm information screens 231-1 through 234-1. Similarly, operation of software buttons 142–143, which in the preferred embodiment are associated with control/navigation, may result in EKG monitor 100 displaying a corresponding one of operation screens 243-1 and 244-1.

It should be appreciated that the screen hierarchy may include any number of levels of screens. For example, each of lower level screens 231-1 through 234-1 and 243-1 have still lower level screens associated therewith, shown here as screens 231-2 through 234-2. Moreover, there may be any number of lower level screens associated with any particular higher level screen. For example, in the illustrated embodiment operation screen 243-1, providing configuration options according to the preferred embodiment, has a plurality of lower level screens, configuration screens 243-2 and 243-3, associated therewith. In contrast, operation screen 244-1, providing user condition diagnostic information according to the preferred embodiment, has no lower level screens uniquely associated therewith.

According to the preferred embodiment, one or more screens are not strictly restricted to hierarchical access and/or may not be uniquely associated with a particular higher level screen. Accordingly, screens presenting general interest information and/or information or functions desired to be readily available, may be available throughout the hierarchy, or portions thereof. For example, glossary screen 201 of the illustrated embodiment, such as may present definitions of terms used with respect to EKG monitor 100, and/or reference information 202, such as may provide instruction and/or general information, may be available from a number of the screens of the preferred embodiment hierarchy. Although such screens may be available from a number of screens in the hierarchy, they may be operable to provide information associated with a particular screen from which they were accessed. For example, glossary screen 201 may provide a definition of a particular word selected upon any screen of the hierarchy from which it has been activated. Similarly, reference information screen 202 may provide context sensitive help and/or general information associated with the context of a particular screen from which it is accessed, if desired.

The highest level screen of the aforementioned hierarchy might be a monitor screen presenting information with respect to currently monitored attributes, as represented by monitor screen 170 of FIG. 1A. Such a screen may provide information with respect to the monitored biotelemetric data, such as graphical representations of lead I (trace 111), lead II (trace 112), and augmented lead aVR (trace 113) and/or alpha numeric representations of monitored attributes (data 122), such as may include the heart rate, the PR interval, the QRS complex, QTc, the QRS axis, the ST segment changes, and/or the like.

This screen may include interpretive information, such as a general status indicator provided by status indicator 121, with respect to the monitored condition. The rhythm interpretation provided by status indicator 121 may display the current rhythm being monitored, whether a normal sinus rhythm or an abnormal rhythm, either atrial or ventricular rhythm, and may have detailed interpretation/diagnostic information associated therewith, such as presented upon the same screen or available in a subsequent screen. In use, a monitor application of EKG monitor 100 may learn the user's normal resting rhythm, even if it is an abnormal rhythm, and recognize when the rhythm changes. Such an analysis of the monitored data may be of particular importance to cardiac patients that frequently go in and out of abnormal rhythms. For example, it would be particularly useful to recognize when a user goes into an abnormal rhythm and alert the user in order to correlate the abnormal rhythm with symptoms, such as for providing an accurate treatment.

One such abnormal rhythm that is encountered by a number of individuals is atrial fibrillation. It is not uncommon for an individual to frequently go in and out of atrial fibrillation. The preferred embodiment EKG monitor 100 with regular use will preferably learn the user's basic rhythm and would alert the user to changes, such as the onset of atrial fibrillation as well as a return to normal sinus rhythm. It should be realized that atrial fibrillation is of particular importance because of the potential for strokes, particularly when the individual returns to a normal sinus rhythm from atrial fibrillation.

Similarly, the ST segment may be monitored for ST segment changes to warn of potential problems with the cardiac circulation. This type of monitored data interpretation may be utilized to warn a user in real-time that he is exceeding his cardiac function capability. Similarly, ST measurement information may be used according to the present invention to provide EKG stress test analysis during physical activity. Accordingly, monitor screen 170 may provide information regarding the monitored condition which has been interpreted to a useful conclusion or aggregation. Moreover, such interpretive information may be utilized to apprise a professional of the condition for further analysis and interpretation.

Alarms are also preferably provided according to the present invention to alert the user and/or others of potentially serious, or other noteworthy, conditions. Preferably, one or more of the monitored attributes and/or the interpretive results have an alarm indicator associated therewith. If an attribute of such biotelemetric data is outside the range of normal, or other window or threshold established according to the present invention, the alarm will alert the user and/or a professional, such as by sounding a tone, flashing an indicator, establishing a communication link with an external host and/or the like.

For example, the embodiment of EKG monitor 100 illustrated in FIG. 1A includes alarm buttons 131–134 corresponding to data 122, trace 111, trace 112, and trace 113 respectively. As mentioned above, alarm buttons 131–134 of the preferred embodiment are software buttons, such as may not only present information with respect to an alarm condition (or lack thereof), but may also provide a user interface, such as to facilitate presenting further information with respect to a particular alarm condition when an alarm button is operated by a user. For example, if data 122 includes a particularly high heart rate for the user of EKG monitor 100, such as may be determined through entry of a high heart rate threshold in a user configuration database and/or as may be determined by historical analysis of data monitored by EKG monitor 100, alarm button 131 would preferably display information with respect to the heart rate being particularly high and prompt the user to go into further screens for more information, definitions, possible causes, possible symptoms, diagnostics, and/or recommendations.

Accordingly, when an alarm condition is detected by EKG monitor 100 in any of data 122, trace 111, trace 112, trace 113, and/or any other monitored attribute (whether currently displayed or not), a corresponding one of alarm buttons 131–134 may preferably change color, flash, or otherwise operate to attract attention, and present information therein, or associated therewith, to indicate the particular condition resulting in alarm. The user may operate the particular one of alarm buttons 131–134 indicating an alarm condition and have displayed a lower level screen with respect to the alarm condition, such as alarm information screens 231-1 through 234-1 and/or detail/recommendation screens 231-2 through 234-2. This further information may explain the alarm condition, provide interpretation of the monitored biotelemetric data, provide a recommended course of action, and/or the like. Of course, rather than awaiting a user to operate a button to display a lower level screen with respect to a particular alarm condition, embodiments of the present invention may operate to automatically display a lower level screen upon one or more alarm conditions, if desired.

In addition to the aforementioned changing of the particular alarm button and presenting of information to indicate the particular condition causing alarm, EKG monitor 100 of the preferred embodiment provides further sensory stimulation to alert the user of the alarm. For example, a tone may be sounded simultaneously with the changing of the alarm button through a speaker, piezoelectric device, or other auditory mechanism (all not shown). Additionally or alternatively, the use of digitally synthesized speech may be used, such as to announce the alarm in a particular language, if desired. Additional or alternative means of notifying a user of an alarm condition useful according to the present invention may include vibration of EKG monitor 100 or some portion thereof to stimulate the user's sense of touch, flashing of a light output by EKG monitor 100 to stimulate the user's sense of sight, and/or the like.

It should be appreciated that notification of an alarm condition is not limited to local stimulus. For example, if a particular alarm condition is of a very serious nature, EKG monitor 100 may establish a communication link with a health care professional and/or rescue personnel in order to summon aid for a user perhaps unable to summon aid for himself. Such a link may utilize the aforementioned wireless communication, perhaps in association with position determining technology such as GPS circuitry of an embodiment of EKG monitor 100.

The use of one or more such means of notification may preferably be selected by a user, such as by using configuration screens 243-1 through 243-3 of the preferred embodiment. For example, a user may select to have a wireless communication link established for particularly serious alarm conditions in order to minimize the risk of being unable to summon help upon the onset of such a condition. Additionally or alternatively, the user may select to have speech notice, perhaps in a language selected specifically to be likely to be understood by bystanders, in order to increase the likelihood of obtaining assistance when needed, such as when traveling abroad.

It should be appreciated that the preferred embodiment monitor screen 170 may provide navigation/control functionality in addition to that associated with the aforementioned alarm buttons. For example, software buttons 141–144 may provide various navigational and/or control functions according to the present invention.

Software button 141 of the preferred embodiment may provide a first aid function to allow a user to alert rescue personnel quickly when distressing symptoms are experienced. Accordingly, it should be appreciated that the preferred embodiment screen hierarchy of FIG. 2 does not show a lower level screen associated with first aid button 141. The preferred embodiment initiates a wireless link with a health care professional or rescue personnel upon operation of this button. Of course, a lower level screen may be associated with operation of this button, such as to show the status of the summon for help. Additionally or alternatively, lower level screens may be accessed to provide instructions as to what first aid measures should be applied, such as through EKG monitor 100 referencing monitored conditions and interpreting those conditions to present a recommended course of first aid treatment. For example, first aid button 141 may provide basic first aid information, including CPR etcetera, for assisting the user or others in an emergency.

Software button 142 of the preferred embodiment may provide help or other reference information to a user. For example, help button 142 of the preferred embodiment may access reference information screen 202 of FIG. 2 to allow a user to navigate an on-line operation manual with respect to EKG monitor 100. Additionally or alternatively, reference button 142 may access reference information screen 202 of FIG. 2 to allow a user to browse an electronic reference volume providing general information with respect to conditions to be monitored by EKG monitor 100 etcetera.

Software button 143 of the preferred embodiment may provides navigation with respect to operational aspects of EKG monitor 100. For example, configuration button 143 of the preferred embodiment may provide access to configuration/settings screen 243-1, perhaps displaying presently selected configurable settings of EKG monitor 100, and/or configuration screens 243-2 and 243-3, perhaps allowing selection of particular configurable aspects of EKG monitor 100.

Software button 144 of the preferred embodiment may provide data interpretation and/or diagnosis of a condition to a user. For example, diagnostic button 144 of the preferred embodiment may cause EKG monitor 100 to give an interpretation of the EKG tracings with definitions, recommended courses of action, and/or the like.

The preferred embodiment of screen 170 provides for navigation of screens using intuitive links, not necessarily represented by buttons as described above. For example, the three leads displayed upon screen 170 might be paused, for example, and a user may be able to select any the complexes displayed to go to a secondary screen to give a description of that particular complex or an abnormality represented thereby.

Although not actually a part of monitor screen 170 of the preferred embodiment, it should be appreciated that hardware button 151 provides an event record button to allow a user to initiate event recording when experiencing particular symptoms and thereby freeze the monitored data displayed upon monitor screen 170. Accordingly, the preferred embodiment of EKG monitor 100 can store data and/or traces, similar to an event recorder, when a user experiences symptoms, such as lightheadedness, or feels palpitations etcetera. This recorded information may be retrieved later, such as by a data download to a host system, by hard copy output, by viewing of EKG monitor 100 by a trained professional, by facsimile transmission, and/or the like, for further professional diagnostic interpretation.

Additionally or alternatively, freezing of such data may be utilized to implement interpretation of the monitored data by EKG monitor 100. Accordingly, operation of a event record button according to the present invention may trigger data interpretation, such as may be displayed upon a lower level screen and/or recorded for later analysis by a trained professional. It should be appreciated that frequently symptoms occur with or without palpitations and it is difficult to correlate the abnormal rhythms with symptoms and, accordingly, the preferred embodiment event recording and interpretation function of EKG monitor 100 may be utilized to assist in making a correlation. For example, if there is an actual arrhythmia or rhythm problem that is causing any particular symptom, EKG monitor 100 would preferably be able to correlate the two with the event recorder.

It should be appreciated that, although described above with reference to a preferred embodiment highest level monitor screen, one or more of the above screen attributes may be present in various other ones of the screens of the preferred embodiment hierarchy. For example, monitored data, whether data 122, trace 111, trace 112, trace 113, or some portion thereof, may be displayed upon a lower level screen, such as an alarm information screen accessed by an alarm button corresponding to the particular monitored data. Similarly, one or more of the aforementioned software buttons may be present in various ones of the lower level screens. For example, first aid button 141 may be present in all, or substantially all, screens to ensure quick availability thereof.

Of course, any or all of the above described attributes may be changed from screen to screen according to the present invention. For example, the information provided in a lower level screen, although corresponding to information presented in a higher level screen, may be formatted differently, may present greater or lesser detail with respect thereto, etcetera. Similarly, the various software buttons available upon various screens in the hierarchy may provide different functionality, be disposed in different locations, be different in number, etcetera.

Even where a same attribute is presented from screen to screen, that attribute may be changed in some way. For example, although hardware button 152 will be present in association with each of the screens of the hierarchy, the functionality of this or other buttons may change according to the context of a particular screen then displayed.

It should be appreciated that the preferred embodiment of the present invention may provide information, data, control, navigation, operation, and/or the like in addition to or in the alternative to that described above. For example, navigation buttons may be provided to allow scrolling and/or paging through information of a screen where that information is unable to be conveniently displayed upon the physical dimensions of display 110.

Any or all of the aforementioned buttons may be implemented in hardware and/or software such that a menu hierarchy may be developed where a few navigation buttons are used to either display software buttons for choices and/or use programmable buttons for different functions depending on the level of the hierarchy.

It should be appreciated that a screen of the preferred embodiment hierarchy accessed at any particular time depends upon such things as a selection by the user, the status of various ones of the monitored biotelemetric data, a screen currently displayed, and/or the like. Accordingly, a particular screen from which monitor screen 170 of the preferred embodiment may proceed may vary depending upon a number of factors.

Directing attention to FIG. 3, an example of a lower level screen format, such as may be accessed by operation of alarm buttons 131–134 of monitor screen 170, is shown. Additionally or alternatively, lower level screens such as screen 370 of FIG. 3 may be accessed by various navigation techniques, such as selecting information displayed upon a higher level screen. For example, high level heart rate information may be displayed upon highest level screen 170 which when selected displays a lower level screen presenting detailed information, definitions, current status, analysis of monitored attributes, instructions, and/or the like with respect to the high level information selected.

Accordingly, the lower level screen format of FIG. 3, presenting screen 370, includes various informational areas, areas 301–307, in which information appropriate to the circumstances in which the screen was accessed may be displayed. For example, area 301 may present identification of the particular monitored biotelemetric data for which the remainder the information of screen 370 is associated. Area 302 may present a current status determined from the monitored biotelemetric data. Areas 303–306 may present further detailed information, such as definitions, symptoms, causes, and recommendations, and/or links to screens providing further detail with respect thereto. Area 307 may present various navigational aids, such as buttons to control scrolling of data, browsing of higher level and/or lower level screens, and/or the like.

Pseudo code for populating the areas of screen 370 according to a preferred embodiment of the present invention is provided in FIG. 4. For example, FIG. 4 presents information with respect to the monitored biotelemetric data "heart rate" as may be accessible by selecting heart rate data of data 122 and/or by selecting alarm button 131 when a heart rate alarm is indicated.

According to the illustrated embodiment "Heart Rate" 401 would be associated with identification area 301 of FIG. 3 for display upon screen 370. Similarly, variables MONITORED DATA 402A, STATUS 402B, INFO 403, SYMPTOMS 404, CAUSES 405, and RECOMMENDATION 406 would be set as provided in FIG. 4 and each be associated with a corresponding one of areas 302–306 of FIG. 3. It should be appreciated that information provided in each such area by the pseudo code of FIG. 4 may include specific information relating to a monitored condition, see e.g. MONITORED DATA 402A, STATUS 402B and RECOMMENDATION 406. Additionally or alternatively, information provided in the areas by the pseudo code of FIG. 4 may include a constant text entry, see e.g., INFO 403, which may or may not include a "jump" or "link" to other information, e.g., "pulse" of INFO 403 may provide a link to a glossary providing further information. The pseudo code of FIG. 4 may additionally or alternatively provide pointers to relevant information to be displayed, see e.g., SYMPTOMS 404 and CAUSES 405, perhaps displaying an excerpt from a reference database of EKG monitor 100 and/or providing "jumps" or "links" to facilitate the display of more detail with respect thereto. Likewise, the pseudo code of FIG. 4 may additionally or alternatively provide calls to common routines or "toolboxes," see e.g., toolbox call 407 associated with area 307, to simplify the implementation of reoccurring functions, such as screen hierarchy navigation tools.

Any or all of the above presented information may provide for associated input by the user. For example, the aforementioned "jumps" or "links" may provide for selection by a user to indicate a desire to jump to the associated information. Similarly, the information of screen 307 may provide for substantive input, such as by allowing a user to input symptoms currently experienced, such as by selecting one or more systems presented by symptoms 404 and/or by inputting a symptom narrative.

It should be appreciated that the pseudo code of FIG. 4 is not limited to populating the areas of screen 370 of FIG. 3. Accordingly, various functions may be performed to provide desired functionality associated with the particular screen displayed. For example, function 408 may provide correlation of one measure of heart rate with another measure of pulse in order to interpret the data for a determination as to whether fibrillation is occurring. Similarly, function 409 may provide correlation of the monitored heart rate with symptoms indicated for storage in a historical database of EKG monitor 100, for interpretation by EKG monitor 100, and/or for analysis by a trained professional. Such correlation, or other functions provided by the present invention, may be utilized in providing information to the user, such as correlation of heart rate with symptoms by function 409 for establishing a value of variable RECOMMENDATION 406 to be displayed to user in area 306.

It should be appreciated that the present invention may operate to provide a number of different analyses using a various biotelemetric information and/or other parameters. For example, a PR interval of greater than 0.20 second may be determined to indicate a 1° atrio-ventricular block, which if not present before may be correlated to ischemia, a new medication, or other available data. QRS greater than 0.12 second may be determined to indicate intra-ventricular conduction delay, such as right bundle branch block or left bundle branch block, which if not present before may be correlated to ischemia, structural heart disease, etcetera. Any pause in electrical activity greater than 2 seconds may be determined to be a significant event which indicates a pacemaker is needed and may be correlated with symptoms on an event recorder for further analysis. QT interval prolongation may be determined to be indicative of ischemia or may be correlated to the use of a new medication and may provide early warning of risk of death due to prolonged QT syndrome. ST segment changes greater than 2 mm may be determined to indicate ischemia if present in 2 or more leads. Isolated premature ventricular contractions in alternating patterns with normal QRS may be determined to indicate a condition known as Bigeminy/Trigeminy. Atrio-ventricular heart block of 1° may be determined from prolonged PR, of 2° may be determined from Type I (Wenkebach) or Type II AV nodal blocks, of 3° may be determined from complete articular/ventricular dissociation with very slow pulse indicates a pacemaker is needed. Articular tachycarda may be determined from a narrow QRS complex. Ventricular tachycardia may be determined from wide QRS complex.

Accordingly, preferred embodiments of the present invention correlate symptoms, such as chest pain/shortness of breath, sweating/cold and clammy/weakness, pain in jaw/neck/shoulder/arm, dizziness/light headed/faintness, palpitation/skipped beats/racing, loss of energy/stamina/fatigue, blue discoloration of the skin/nausea/vomiting, pedal edema, shortness of breath on exertion/shortness of breath when laying prone, and the like, with EKG abnormalities. Additionally or alternatively, preferred embodiments of the present invention correlate EKG findings with other biotelemetric parameters, such as pulse, blood pressure, respiratory rate, oxygen saturation, etcetera. Using such correlation techniques, embodiments of the present invention may be utilized to provide analysis, recommendations, and/or diagnostic information to users.

From the above example, it should be appreciated that the information provided on a secondary or lower level screen may include some initial basic information, and that the screen may also present a pathway to further tertiary or yet lower level screens with additional information. For example, any particular secondary screen may have a symptom feature with basic symptoms from which the user could go into a tertiary screen which describes the particular symptoms of that particular feature in more detail. Such tertiary screens may include specific detail, such as symptoms which may correlate with the rhythms being monitored including chest pains, shortage of breath, dizziness, nausea, etcetera, and may also prompt the user to go to additional screens with causes of symptoms, recommendations, and/or potential dangers associated with any abnormalities monitored.

It should be appreciated that screen formats in addition to or in the alternative to that of FIG. 3 may be utilized by various ones of the screens according to the present invention. For example, another lower level or secondary screen may present a primary interpretation of a biotelemetric being monitored, such as to present a primary interpretation of a EKG trace displayed. This screen might provide identification of the biotelemetric for which information is being provided as well as to provide information with respect thereto. Such information in the above EKG trace example may include identification of the rhythm, providing a definition or the meaning of the rhythm, provide potential causes of the rhythm and any symptoms that are usually associated with the rhythm, and/or provide recommendations. Historical information may be provided, such as an indication as to whether the user has ever had that particular rhythm in previous recordings.

Additionally or alternatively, basic informational screens may be provided according to the present invention, such as may be accessed from any of the above screens for further information, and/or as may accessed outside of the navigational flow described above. Access to such basic information screens outside of the aforementioned navigational flow may be desirable to provide general information to a user without having to navigate specific screens. Basic informational screens available according to a preferred embodiment of the present invention could include risk factors for heart disease, basic first aid information including CPR for the general user, definitions or glossary screens that would give basic definitions of all the terms and phrases, etcetera.

A basic information screen which may be of particular usefulness according to a preferred embodiment of the present invention is one in which the placement of the various probes upon the body is illustrated in order to aid a lay-user in the proper deployment of the probes. Such a screen may include not only a graphical representation of where to place the probes, but may also provide information with respect to when a particular pattern should be selected over another of the available patterns. In situations where various probe deployment patterns are possible, as described above with respect to the 12 EKG lead positions, such a screen may not only illustrate the proper placement of the probes, but may also operate to configure the monitor for use with a particular selected probe deployment pattern.

In addition to the aforementioned screens presenting substantive information with respect to biotelemetry, there may be additional screens utilized according to the present invention, such as a legal screen providing limitations on the use of the device as well as disclaimers. For example, on a legal disclaimer screen, an important feature may be to clearly warn the user that the device does not provide an absolute diagnostic tool capable of replacing consultation with a trained professional.

Preferred embodiments of the present invention provide a portable unit which is affordable enough to facilitate large scale deployment. Accordingly, preferred embodiments may be provided using the aforementioned existing PDA platforms. Such embodiments may include software defining operation as described herein operable upon a particular host PDA platform. Interfaces or other components may be provided for use according to the present invention by coupling expansion circuitry to existing PDA interfaces, such as a CF FLASH slot or other such interface. For example, an expansion "sleeve" may be developed to include all or some of the interface functionality of interface 13 shown in FIG. 1B which interfaces with the expansion port of the IPAQ SERIES 3600 POCKET PC available from Compaq Computer Corporation to thereby provide a portable unit of the present invention.

Figure 5A:
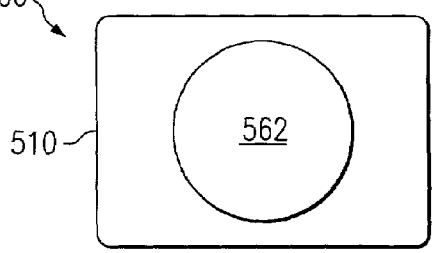
FIGS. 5A–5C show a biotelemetry monitoring device according to an alternative embodiment of the present invention.
Figure 5B:
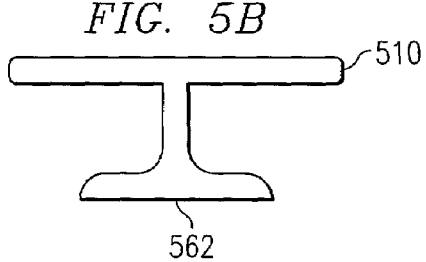
Figure 5C:
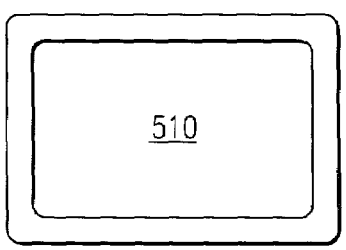

However, preferred embodiments of the present invention, although utilizing circuitry and other components of such an existing platform, provide a solution in which the form factor of the device is unique to the present application, such as to provide a sufficiently ruggadized case enclosing all components thereof. Moreover, the form factor of the present invention is not limited to that represented in the illustrated embodiment of FIG. 1A. For example, embodiments of the present invention may provide a device, such as may include the features and functions described above or portions thereof, in a form factor configured for a particular use. Directing attention to FIG. 5 an alternative embodiment biotelemetry monitor according to the present invention is shown as EKG monitor 500.

EKG monitor 500 of the illustrated embodiment provides a portable unipolar chest lead monitor. Preferably, unipolar lead 562 is provided integrally with monitor 510 to facilitate placing of EKG monitor 500 upon one of the aforementioned unipolar chest lead locations for displaying a corresponding trace upon monitor 510, much like a physician would place a stethoscope upon a patient. The EKG monitor may preferably be used and/or moved to any of the six chest lead positions to give the EKG display of each lead. Preferably, screens would be available to show the current rhythm associated with the particular lead being monitored. EKG monitor 500 may provide additional processing as discussed above, such as to record monitored biotelemetric data, to interpret data, to provide information, etcetera.

EKG monitor 500 may preferably stand alone as an independent unit to give the rhythm of anyone of the six chest lead positions. Additionally or alternatively, EKG monitor 500 may provide a probe which may be interfaced with another system, such as to provide a lead of EKG monitor 100 described above, or to provide an enhanced stethoscope probe, etcetera. For example, EKG monitor 500 may be attached to a stethoscope to enable a physician to simultaneously listen to the heart sound and view the unipolar chest leads EKG trace. Accordingly, it should be appreciated that EKG monitor 500 may include biotelemetric transducers in addition to or in the alternative to a unipolar electrodes, such as a diaphragm for receiving sound energy.

Although preferred embodiments of the present invention have been discussed above with respect to electrocardiogram monitoring, the present invention is not so limited. Embodiments of the present invention may provide biotelemetry monitoring and data analysis for a variety of uses. For example, an alternative embodiment of the present invention provides a low cost, portable, and interpretive polygraph device, such as may be used in the field by law enforcement officers.

Moreover, preferred embodiments of the present invention may provide biotelemetry monitors adapted or adaptable for a plurality of uses. For example, the aforementioned processor platform may be provided with an application program defining operation as an EKG monitor of the present invention and an application program defining operation as an interpretive polygraph device of the present invention. Particular biometric probes may be coupled to the biotelemetry monitor depending upon the current use to which the device is to be put.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A portable electrocardiograph monitor system comprising:
    a display providing for display of both textual and graphical information;
    a screen hierarchy for presenting information upon said display;
    a probe interface for receiving 3 leads of electrocardiograph data from a plurality of probes;
    a processor operable to accept data received via said probe interface and present at least a portion thereof upon said display, wherein a first screen of said screen hierarchy provides said at least a portion of said data presented upon said display; and
    an alarm for providing audible instructions to a patient relating to interpreted electrocardiograph data; and
    wherein said first screen further provides alarm information associated with said at least a portion of said electrocardiograph data displayed upon said display, wherein a second screen of said screen hierarchy provides alarm specific details associated with said alarm information, and wherein said second screen is accessible from said first screen by operation of an alarm button by a user.

2. The system of claim 1, wherein said display comprises a touch screen element for accepting user input.

3. A portable electrocardiograph monitor system comprising:
    a display providing for display of both textual and graphical information;
    a screen hierarchy for presenting information upon said display;
    a probe interface for receiving 3 leads of electrocardiograph data from a plurality of probes;
    a processor operable to accept data received via said probe interface and present at least a portion thereof upon said display, wherein a first screen of said screen hierarchy provides said at least a portion of said data presented upon said display; and
    an alarm for providing audible instructions to a patient relating to interpreted electrocardiograph data; and
    an event recorder operable to record data received via said probe interface for later access wherein said event recorder is controlled to record an event upon input by a user, wherein said input by a user is provided by operation of an event recorder button available to said user throughout a plurality of screens of said screen hierarchy.

4. The system of claim 3, wherein said event recorder is controlled to record an event upon interpretation of said data received via said probe interface by said processor.

5. The system of claim 4, wherein said interpretation provides a determination that said data received via said probe interface indicates an irregularity.

6. The system of claim 4, wherein said interpretation provides a determination that said data received via said probe interface is abnormal as compared to a user's normal data as monitored by said system.

7. A portable electrocardiograph monitor system comprising:
    a display providing for display of both textual and graphical information;
    a screen hierarchy for presenting information upon said display;
    a probe interface for receiving 3 leads of electrocardiograph data from a plurality of probes;
    a processor operable to accept data received via said probe interface and present at least a portion thereof upon said display, wherein a first screen of said screen hierarchy provides said at least a portion of said data presented upon said display; and an alarm for providing audible instructions to a patient relating to interpreted electrocardiograph data; and a reference database storing general information for use with respect to electrocardiograms.

8. The system of claim 7, wherein said general information comprises a glossary of terms.

9. A portable electrocardiograph monitor system comprising:

a display providing for display of both textual and graphical information;

a screen hierarchy for presenting information upon said display;

a probe interface for receiving 3 leads of electrocardiograph data from a plurality of probes;

a processor operable to accept data received via said probe interface and present at least a portion thereof upon said display, wherein a first screen of said screen hierarchy provides said at least a portion of said data presented upon said display; and an alarm for providing audible instructions to a patient relating to interpreted electrocardiograph data; and a database of context sensitive help with respect to use of said system.

* * * * *